(12) United States Patent
Sadda et al.

(10) Patent No.: US 9,226,654 B2
(45) Date of Patent: Jan. 5, 2016

(54) SYSTEMS AND METHODS FOR AUTOMATED CLASSIFICATION OF ABNORMALITIES IN OPTICAL COHERENCE TOMOGRAPHY IMAGES OF THE EYE

(75) Inventors: SriniVas R. Sadda, Pasadena, CA (US); Paul F. Stetson, Piedmont, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 788 days.

(21) Appl. No.: 13/457,349

(22) Filed: Apr. 26, 2012

(65) Prior Publication Data

US 2012/0274898 A1   Nov. 1, 2012

Related U.S. Application Data

(60) Provisional application No. 61/518,186, filed on Apr. 29, 2011.

(51) Int. Cl.
*A61B 3/14* (2006.01)
*A61B 3/10* (2006.01)
*G01B 9/02* (2006.01)
*G06T 7/00* (2006.01)

(52) U.S. Cl.
CPC ............ *A61B 3/102* (2013.01); *G01B 9/02044* (2013.01); *G01B 9/02083* (2013.01); *G01B 9/02091* (2013.01); *G06T 7/0012* (2013.01); *G06T 2207/10101* (2013.01); *G06T 2207/20081* (2013.01); *G06T 2207/30041* (2013.01)

(58) Field of Classification Search
CPC ........ A61B 3/1015; A61B 3/103; A61B 3/12; A61B 3/14; A61B 6/032; G06T 11/006

USPC .......................................... 359/205, 206, 246
See application file for complete search history.

(56) References Cited

U.S. PATENT DOCUMENTS

| | | |
|---|---|---|
| 4,838,679 A | 6/1989 | Bille |
| 5,293,871 A | 3/1994 | Reinstein et al. |
| 5,562,095 A | 10/1996 | Downey et al. |
| 5,861,955 A | 1/1999 | Gordon |
| 6,165,142 A | 12/2000 | Bar |
| 6,260,968 B1 | 7/2001 | Stark et al. |

(Continued)

FOREIGN PATENT DOCUMENTS

EP   0415683 A2   3/1991

OTHER PUBLICATIONS

Choma et al., "Sensitivity Advantage of Swept Source and Fourier Domain Optical Coherence Tomography", Optics Express, vol. 11, No. 18, Sep. 8, 2003, pp. 2183-2189.

(Continued)

*Primary Examiner* — James Greece
(74) *Attorney, Agent, or Firm* — Morrison & Foerster LLP

(57) ABSTRACT

Systems and methods for classifying abnormalities within optical coherence tomography images of the eye are presented. One embodiment of the present invention is the classification of pigment epithelial detachments (PEDs) based on characteristics of their internal reflectivity, size and shape. The classification can be based on selected subsets of the data located within or surrounding the abnormalities. Training data can be used to generate the classification scheme and the classification can be weighted to highlight specific classes of particular clinical interest.

23 Claims, 5 Drawing Sheets

(56) References Cited

U.S. PATENT DOCUMENTS

| | | | |
|---|---|---|---|
| 6,609,793 | B2 | 8/2003 | Norrby et al. |
| 7,145,661 | B2 | 12/2006 | Hitzenberger |
| 7,194,117 | B2 | 3/2007 | Kaufman et al. |
| 7,301,644 | B2 | 11/2007 | Knighton et al. |
| 7,364,296 | B2 | 4/2008 | Miller et al. |
| 7,365,856 | B2 | 4/2008 | Everett et al. |
| 7,466,423 | B2 | 12/2008 | Podoleanu et al. |
| 7,616,799 | B2 | 11/2009 | Ramamurthy et al. |
| 7,744,221 | B2 * | 6/2010 | Wei et al. .................... 351/246 |
| 7,830,525 | B2 | 11/2010 | Buckland et al. |
| 7,884,945 | B2 | 2/2011 | Srinivasan et al. |
| 7,901,080 | B2 | 3/2011 | Hauger et al. |
| 2003/0199769 | A1 | 10/2003 | Podoleanu et al. |
| 2004/0133112 | A1 | 7/2004 | Rajadhyaksha |
| 2005/0048044 | A1 | 3/2005 | Schwartz et al. |
| 2005/0096515 | A1 | 5/2005 | Geng |
| 2005/0254009 | A1 | 11/2005 | Baker et al. |
| 2006/0066869 | A1 | 3/2006 | Ueno et al. |
| 2006/0119858 | A1 | 6/2006 | Knighton et al. |
| 2006/0164639 | A1 | 7/2006 | Horn et al. |
| 2006/0164653 | A1 | 7/2006 | Everett et al. |
| 2006/0187462 | A1 | 8/2006 | Srinivasan et al. |
| 2006/0228011 | A1 | 10/2006 | Everett et al. |
| 2007/0012886 | A1 | 1/2007 | Tearney et al. |
| 2007/0025642 | A1 | 2/2007 | Buckland et al. |
| 2007/0030483 | A1 | 2/2007 | Everett et al. |
| 2007/0103693 | A1 | 5/2007 | Everett et al. |
| 2007/0115481 | A1 | 5/2007 | Toth et al. |
| 2007/0216909 | A1 | 9/2007 | Everett et al. |
| 2011/0299034 | A1 | 12/2011 | Walsh et al. |
| 2012/0075584 | A1 | 3/2012 | Stetson |
| 2013/0281841 | A1 | 10/2013 | Everett et al. |

OTHER PUBLICATIONS

Chung et al., "Choroidal Thickness in Polypoidal Choroidal Vasculopathy and Exudative Age-related Macular Degeneration", Ophthalmology, vol. 118, No. 5, May 2011, pp. 840-845.
Gregori et al., "Imaging Drusen With Spectral Domain Optical Coherence Tomography", Invest Ophthalmol Vis Sci, vol. 49, E-Abstract 4234, 2008, 2 pages.
Hartnett et al., "Classification of Retinal Pigment Epithelial Detachments Associated with Drusen", Graefes Arch Clin Exp Ophthalmol, vol. 230, 1992, pp. 11-19.
Khanifar et al., "Drusen Ultrastructure Imaging with Spectral Domain Optical Coherence Tomography in Age-related Macular Degeneration", Ophthalmology, vol. 115, No. 11, Nov. 2008, pp. 1883-1890.
Lee et al., "Automated Characterization of Pigment Epithelial Detachment using Optical Coherence Tomography", 2011 the Association for Research in Vision and Ophthalmology Inc. Poster Abstract Program #1317, Poster #A254, 2011, 27 pages.
Leitgeb et al., "Ultrahigh Resolution Fourier Domain Optical Coherence Tomography", Optics Express, vol. 12, No. 10, May 17, 2004, pp. 2156-2165.
Lumbroso et al., "Morphologic Differences, According to Etiology, in Pigment Epithelial Detachments by Means of En Face Optical Coherence Tomography", Retina, The Journal of Retinal and Vitreous Diseases, vol. 31, No. 3, 2011, pp. 553-558.
Zayit-Soudry et al., "Retinal Pigment Epithelial Detachment", Survey of Ophthalmology, vol. 52, No. 3, May-Jun. 2007, pp. 227-243.
Notice of Allowance received for U.S. Appl. No. 11/717,263, mailed on Mar. 23, 2010, 6 pages.
Non Final Office Action received for U.S. Appl. No. 12/709,234, mailed on Feb. 16, 2011, 6 pages.
Notice of Allowance received for U.S. Appl. No. 12/709,234, mailed on Jul. 28, 2011, 10 pages.
Non Final Office Action received for U.S. Appl. No. 12/822,054, mailed on Apr. 5, 2011, 12 pages.
Notice of Allowance received for U.S. Appl. No. 12/822,054, mailed on Jul. 26, 2011, 7 pages.
Final Office Action received for U.S. Appl. No. 13/240,701, mailed on Jul. 15, 2013, 9 pages.
Non Final Office Action received for U.S. Appl. No. 13/240,701, mailed on Dec. 21, 2012, 9 pages.
Non-Final Office Action received for U.S. Appl. No. 13/240,701, mailed on Nov. 7, 2013, 9 pages.
Notice of Allowance received for U.S. Appl. No. 13/240,701, mailed on Feb. 20, 2014, 10 pages.
Notice of Allowance received for U.S. Appl. No. 13/283,445, mailed on Feb. 23, 2012, 10 pages.
Notice of Allowance received for U.S. Appl. No. 13/488,280, mailed on Dec. 10, 2012, 10 pages.
Non Final Office Action received for U.S. Appl. No. 13/787,557, mailed on Mar. 21, 2014, 8 pages.
Knighton et al., U.S. Appl. No. 60/632,387, filed Dec. 2, 2004, titled "Enhanced Optical Coherence Tomography for Anatomical Mapping", 26 pages.
Adaikkappan et al., "Evaluation of Carotid Atherosclerosis by B'Mode Ultrasonographic Study in Hypertensive Patients Compared with Normotensive Patients", Ind. J. Radiol. Imag., vol. 12, No. 3, 2002, pp. 365-368.
Alam et al., "Clinical Application of Rapid Serial Fourier-Domain Optical Coherence Tomography for Macular Imaging", Ophthalmology, vol. 113, No. 8, Aug. 2006, pp. 1425-1431.
Bartsch et al., "Optical Coherence Tomography: Interpretation Artifacts and New Algorithm", Proceedings of SPIE, vol. 5370, 2004, pp. 2140-2151.
Burgoyne et al., "Three-Dimensional Reconstruction of Normal and Early Glaucoma Monkey Optic Nerve Head Connective Tissues", Investigative Ophthalmology & Visual Science, vol. 45, No. 12, Dec. 2004, pp. 4388-4399.
Carl Zeiss Meditec, Inc., "Stratus OCT1M—Model 3000", User Manual by Carl Zeiss Meditec, Inc., 2004, 191 pages.
Costa et al., "Retinal Assessment Using Optical Coherence Tomography", Progress in Retinal and Eye Research, vol. 25, 2006, pp. 325-353.
De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.
Fercher et al., "Optical Coherence Tomography—Principles and Applications", Reports on Progress in Physics, vol. 66, 2003, pp. 239-303.
Guirao et al., "Corneal Wave Aberration from Videokeratography: Accuracy and Limitations of the Procedure", J. Opt. Soc. Am. A., vol. 17, No. 6, Jun. 2000, pp. 955-965.
Heidelberg Engineering, "Bringing Two Views Together", Spectralis HRA + OCT, Brochure by Heidelberg Engineering, 2006, 6 pages.
Hitzenberger et al., "Three-Dimensional Imaging of the Human Retina by High-Speed Optical Coherence Tomography", Optics Express, vol. 11, No. 21, Oct. 20, 2003, pp. 2753-2761.
Ishikawa et al., "Macular Segmentation with Optical Coherence Tomography", Investigative Ophthalmology & Visual Science, vol. 46, No. 6, Jun. 2005, pp. 2012-2017.
Koozekanani et al., "Tracking the Optic Nervehead in OCT Video Using Dual Eigenspaces and an Adaptive Vascular Distrubution Model", IEEE Transactions on Medical Imaging, vol. 22, No. 12, Dec. 2003, pp. 1519-1536.
Leitgeb et al., "Performance of Fourier Domain vs. Time Domain Optical Coherence Tomography", Optics Express, vol. 11, No. 8, Apr. 21, 2003, pp. 889-894.
Mujat et al., "Retinal Nerve Fiber Layer Thickness Map Determined from Optical Coherence Tomography Images", Optics Express, vol. 13, No. 23, Nov. 14, 2005, pp. 9480-9491.
Nassif et al., "In Vivo Human Retinal Imaging by Ultrahigh-Speed Spectral Domain Optical Coherence Tomography", Optics Letters, vol. 29, No. 5, Mar. 1, 2004, pp. 480-482.
Nassif et al., "In Vivo High-Resolution Video-Rate Spectral-Domain Optical Coherence Tomography of the Human Retina and Optic Nerve", Optics Express, vol. 12, No. 3, Feb. 9, 2004, pp. 367-376.
"OTI OCT/SLO Combination Imaging System", OTI Ophthalmic Technologies Inc, 2005, 6 pages.
"RTVue-100—In-Vivo Histology (Fourier Domain OCT)", Optovue Inc., 2006, 6 pages.

(56) References Cited

OTHER PUBLICATIONS

"OCT/SLO Combination Imaging System User Manual", OTI Ophthalmic Technologies Inc., 2005, 79 pages.

Paunescu et al., "Reproducibility of Nerve Fiber Thickness, Macular Thickness, and Optic Nerve Head Measurements Using StratusOCT", Investigatative Ophthalmology & Visual Science, vol. 45, No. 6, Jun. 2004, pp. 1716-1724.

Sadda et al., "Automated Detection of Clinically Significant Macular Edema by Grid Scanning Optical Coherence Tomography", Ophthalmology, vol. 113, No. 7, Jul. 2006, pp. 1187-1196.

Schmidt-Erfurth et al., "Three-Dimensional Ultrahigh-Resolution Optical Coherence Tomography of Macular Diseases", Investigatative Ophthalmology & Visual Science, vol. 46, No. 9, Sep. 2005, pp. 3393-3402.

Webb, Robert H., "Confocal Optical Microscopy", Rep. Prog. Phys., vol. 59, 1996, pp. 427-471.

Wilkins et al., "Characterization of Epiretinal Membranes Using Optical Coherence Tomography", Ophthalmology, vol. 103, No. 12, Dec. 1996, pp. 2142-2151.

Zhou et al., "Mapping Retinal Thickness and Macular Edema by High-Speed Three-Dimensional Optical Coherence Tomography", Proceedings of SPIE, vol. 5314, 2004, pp. 119-125.

\* cited by examiner

SYSTEMS AND METHODS FOR AUTOMATED CLASSIFICATION OF ABNORMALITIES IN OPTICAL COHERENCE TOMOGRAPHY IMAGES OF THE EYE

PRIORITY

This application claims priority to U.S. Provisional Application Ser. No. 61/518,186 filed Apr. 29, 2011 hereby incorporated by reference.

TECHNICAL FIELD

One or more embodiments of the present invention relate to analysis of optical coherence tomography data of the eye. In particular, it is an aspect of the present invention to automatically characterize and classify abnormalities in the eye. The invention can be applied to the classification of pigment epithelial detachments.

BACKGROUND

Detachment of the retinal pigment epithelium is characteristic of a variety of chorio-retinal diseases including age related macular degeneration (see for example Zayit-Soudry et al. "Retinal pigment epithelial detachment" Surv Ophthalmol 52(3): 227-243 2007). Various types of pigment epithelial detachments (PEDs) have been identified including serous, fibrovascular, and drusenoid among others (see for example Hartnett et al. "Classification of retinal pigment epithelial detachments associated with drusen", *Graefes Arch Clin Exp Ophthalmol.* 1992; 230(1):11-90. Optical coherence tomography (OCT) has provided a way to visualize, segment and classify PEDs. Previous work has categorized PEDs and drusen manually (see for example Lumbroso et al. "Morphologic Differences, According To Etiology, in Pigment Epithelial Detachments By Means of En Face Optical Coherence Tomography", *Retina* 31 (3): 553-558 2011, Hartnett et al. "Classification of retinal pigment epithelial detachments associated with drusen", *Graefes Arch Clin Exp Ophthalmol.* 1992; 230(1):11-9, Khanifar et al. "Drusen ultrastructure imaging with spectral domain optical coherence tomography in age-related macular degeneration", *Ophthalmology.* 2008 November; 115(11):1883-90), but this is a time consuming process requiring expert clinical input. A system and method capable of automatically segmenting and classifying PEDs would be highly desirable.

A segmentation map of RPE Elevations may provide too many drusen to be easily examined by individual B-scan inspection. An automated screening strategy, however, can give a quick assessment of the internal and surface characteristics of RPE elevations and nearby structures, which may provide a risk assessment for the development of advanced complications such as manifest fibrovascular infiltration or cellular atrophy among others.

SUMMARY

It is an object of the present invention to provide an automated way to characterize and classify abnormalities in optical coherence tomography image data, based on analysis of the intensity characteristics of the OCT data within the boundaries of the abnormality as well as the shape of the abnormality. The description and figures are directed towards the classification and characterization of pigment epithelial detachments (PEDs) but the basic concept could equally be applied to other abnormalities within the eye such as polypoidal choroidal vasculopathy (PCV), sub-retinal fluid, tumors, lesions such as hemangiomas and/or nevi, cysts, drusen, optic disc drusen or any situation wherein the layers of the eye are locally distorted from their typical separation and characteristics of the internal reflectivity of the abnormality as well as the size and shape of the abnormality could be used to generate automated classification guidelines. The invention could also be applied to analysis of tissues surrounding the abnormality that may be affected by the abnormality.

A preferred embodiment of the present invention analyzes OCT image data using a segmentation of the RPE and a baseline to define the locations of the PEDs. The image data are normalized in intensity to compensate for shadows from overlying structures and the image intensity within the PEDs and the curvature of the RPE over the detachments are analyzed for evidence of risk for development of advanced complications. Each A-scan is analyzed based on the distribution of intensity within the A-scan, then the results for the individual A-scans in a PED are combined and analyzed for each PED to give an indicator of risk for development of advanced complications and an indicator of the confidence in the risk assessment.

DETAILED DESCRIPTION

The detailed description is directed towards a specific implementation of the invention. It will be obvious to one skilled in the art that various implementations can be imagined that would still fit in the general scope of the invention. Each step will now be described in detail.

Data Collection:

The invention involves analysis of data from an optical coherence tomography (OCT) system. OCT is a non-invasive, in-vivo imaging technique that is based on the back-scatter or reflectivity of light in a medium. OCT is particularly valuable in ophthalmic examinations, where the beam of light produced by the OCT device scans the eye through the pupil and the image formation process records the back-scattering profile of the light at each location. The intensity of the back-scattered light is indicative of the scattering properties of the tissue and tissue boundaries, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice.

Several implementations of OCT have been developed including time domain (TD-OCT) and frequency domain (spectral domain (SD-OCT) and swept-source (SS-OCT)).

Figure 1:
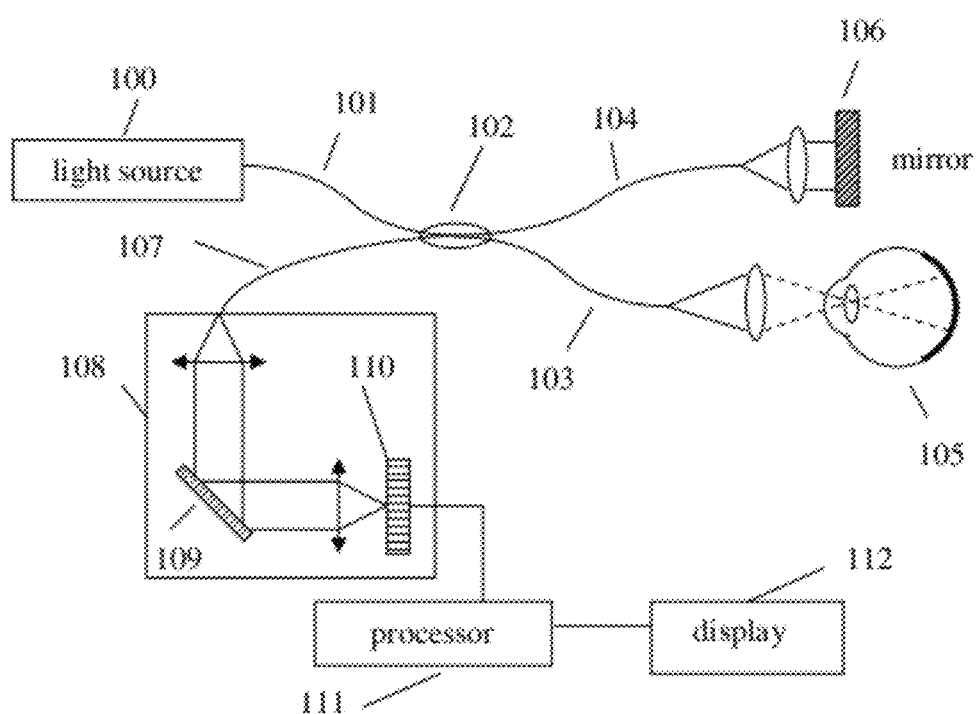
FIG. 1 is a block diagram of a spectral-domain optical-coherence tomography system.

FIG. 1 shows a basic block diagram for a spectrometer based SD-OCT system. The light source 100 provides broad bandwidth light to a short length of an optical fiber 101 to an input port of a fiber optic coupler 102, which splits the incoming light beam into the two arms of an interferometer. The two arms each have a section of optical fiber 103 and 104 that guides the split light beam from the fiber coupler 102 to the eye of a patient 105 and a reference reflector 106 respectively. For both the sample arm and the reference arm, at the terminating portion of each fiber, there may be a module containing optical elements to collimate or focus or scan the beam. The returned light waves from the sample 105 and the reference reflector 106 are directed back through the same optical path of the sample and reference arms and are combined in fiber coupler 102. A portion of the combined light beam is directed through a section of optical fiber 107 from the fiber coupler 102 to a spectrometer 108. Inside the spectrometer, the light beam is dispersed by a grating 109 and focused onto a detector array 110. The collected data is sent to a processor 111 and the resulting processed data can be displayed on a display 112 or stored in memory for future reference and processing. Although the system of FIG. 1 includes a reflective reference arm, those skilled in the art will understand that a transmissive reference arm could be used in its place.

The interference between the returned light waves from the sample and reference arms causes the intensity of the combined light to vary across the spectrum. The Fourier transform of the interference spectrum reveals the profile of scattering intensities at different path lengths, and therefore scattering as a function of depth in the sample (see for example Leitgeb et al., "Ultrahigh resolution Fourier domain optical coherence tomography," *Optics Express* 12(10):2156 2004). The profile of scattering as a function of depth is called an axial scan (A-scan or A-line). A set of A-scans measured at neighboring locations in the sample produces a cross-sectional image (tomogram or B-scan) of the sample. Note that the principle of operation of a tunable laser based swept source OCT is very similar to that of a spectrometer based spectral domain OCT system (see for example, Choma et al. "Sensitivity advantage of swept source and Fourier domain optical coherence tomography." *Optics Express* 11(18): 2183-2189 2003), hence the spectral domain OCT system for obtaining the 3D image data set can also be a swept source OCT system or any type of imaging system that provides visualization of the retinal layers in three dimensions.

OCT data of high transverse resolution is desired. The data described herein was acquired using based a 512×128 Macular cube scan protocol in the Cirrus HD OCT (Carl Zeiss Meditec, Inc.) but any scan pattern capable of generating data capable of visualizing PEDs in three-dimensions can be used.

Segmentation and Data Selection:

The OCT data is segmented to identify the boundaries of the abnormalities within the data. In a preferred embodiment, the data is segmented to give the location of the retinal pigment epithelium (RPE), the inner limiting membrane (ILM), and with a segmentation or RPE curve fit that gives a lower boundary for the pigment epithelial detachments (PEDs) in the image data (see for example Gregori et al. "Imaging drusen with spectral domain optical coherence tomography" Invest Ophthalmol Vis Sci 49(E-Abstract 4234) 2008). One such segmentation is provided by the OCT RPE Elevation Analysis Tool included in the Cirrus HD OCT instrument. Other segmentations can be envisioned by one skilled in the art. The top boundary of the region to be analyzed is taken as the RPE segmentation plus a certain offset to avoid including parts of the RPE due to segmentation bias or error. Similarly the bottom boundary of the region to be analyzed is taken as the Baseline of the RPE Elevation plus an offset to ensure that sufficient data, possibly even below the Bruch's membrane, are included. To ensure sufficient data for robust analysis, only the A-scans with greater than 20 pixels between these boundaries are used. The method of the present invention is designed to be as robust as possible to small errors in segmentation.

Normalization:

Normalization can be applied to the image data prior to analysis to account for inter-individual variability in signal strength and scan intensities. One such normalization will now be described; others can be envisioned by those skilled in the art. To compensate the image data for shadowing or inter-scan variability, the intensity of the image in the vitreous and at the level of the RPE segmentation is estimated. In one embodiment, for each A-scan, the median value of the intensity above the ILM segmentation is used to estimate a local intensity for the vitreous background signal, and the median intensity within a window 10 microns above and below the RPE segmentation is used to estimate the local intensity of the RPE. These local intensity estimates are smoothed over an 82×141 micron window (7 horizontal pixels×3 vertical pixels) to reduce fluctuation in these values. The RPE intensity estimates are then constrained to be a minimum of 10 grayscale levels above the estimates of vitreous intensity. Areas where the RPE Elevation is found to be at least 40 microns are then linearly rescaled so that the estimated vitreous intensity is at zero and the estimated RPE intensity is at 100. The resulting normalized image data is clipped to a grayscale range of 0-255. Areas where the RPE Elevation is found to be below 40 microns are excluded from further analysis. Alternative methods for normalizing and isolating the abnormalities within an OCT data set can be readily envisioned by those skilled in the art.

Analysis of Image Intensity and Lesion Shape:

After the data has been segmented to identify the boundaries of the abnormality and normalized if desired, one or more representative values of the intensity data located within the boundaries of the abnormality are generated. The representative values can be determined for the selected data in its entirety or can be determined for smaller subsets of the selected data. In the preferred embodiment, two representative values are determined for the PED portion of each normalized A-scan in the PED: the mean values of the image intensity and the RPE curvature (as measured by the Laplacian of the RPE segmentation depth). Embodiments of more than two representative values might also prove valuable. The representative values can be smoothed laterally, i.e. by using a 7×3-pixel window.

One skilled in the art would realize that the mean values of image intensities or of features used for the characterization may be alternatively realized by other measures such as the median, trimmed mean, or weighted mean. RPE curvature may alternatively be measured by the mean curvature, by the sum of the absolute values of the second differentials of the RPE depth with respect to the lateral coordinates, or other methods based on lateral derivatives of RPE segmentation depth.

Representative values could also include standard deviation of the intensity, skewness or kurtosis of the image intensities inside the PED, or the mean, median, other measure of average, deviation, skewness or kurtosis of the image intensities above the PED. The size of an abnormality may also help characterize the type of abnormality or the risk posed by an abnormality. Mean size of a group of abnormalities or a measure of the deviation in sizes may help characterize the abnormalities individually or collectively.

Representative values can be calculated for any number of points or groups of points within the abnormality. While a single representative value could be determined for all the intensity data within a single abnormality, as will be described in further detail below, it is possible to combine representative values determined on partial subsets of the data within an abnormality to categorize the entire abnormality or assess the level of confidence with the categorization.

Categorization:

Next, a categorization scheme is developed based on qualities of the data as characterized by the representative values. In a preferred embodiment, individual A-scans are categorized as having the characteristics of serous, drusenoid, fibrovascular PED types, based on rules derived empirically from a training set of OCT data using the mean and RPE curvature as representative values. The training set was a set of OCT data with abnormalities manually classified by a human grader. It consisted of 18 total cases with 5 predominantly drusenoid, 2 predominantly serous, and 11 predominantly fibrovascular. The developed categorization is:

If mean <30→then "Serous"
If mean >30 & RPE curvature >4.4/mm→then "Drusenoid"
If mean >30 & RPE curvature <4.4/mm→then "Fibrovascular"

An alternative categorization developed based on the mean and standard deviation of the intensity data within the boundaries of PEDs is:

If mean <30→then "Serous"
If mean >60 & stdev <30→then "Drusenoid"
If mean >30 & (mean <60|stdev >30)→then "Fibrovascular"

Here, standard deviation provides a measure of the uniformity of the intensity. Serous PEDs are categorized based on their low internal reflectivity. Fibrovascular PEDs are categorized based on either being of medium internal reflectivity or medium to high intensity but heterogeneous reflectivity. Drusenoid PEDs are of high and homogeneous internal reflectivity.

The categorization can be applied to representative values generated from individual A-scans, the intensity of the PED in its entirety, or any subset of data in between. The categorization can be weighted to enhance classification of a particular type of abnormality. In this case, it was desirable to enhance the sensitivity to detect and classify fibrovascular PEDs, since they may be of more clinical importance than other types of PEDs.

Figure 2:
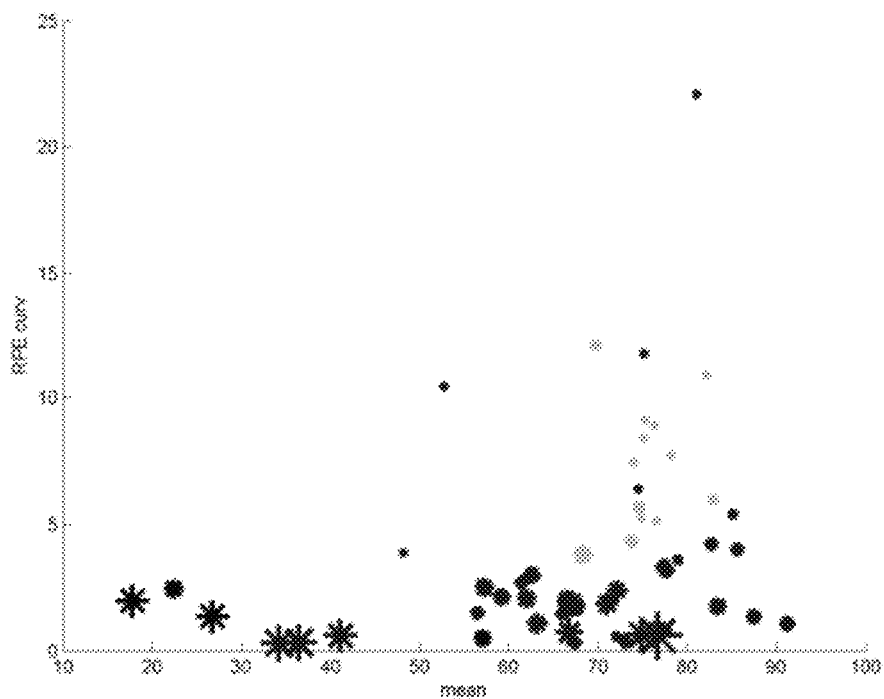
FIG. 2 shows one PED classification method of the present invention applied to a set of training data.
Figure 3:
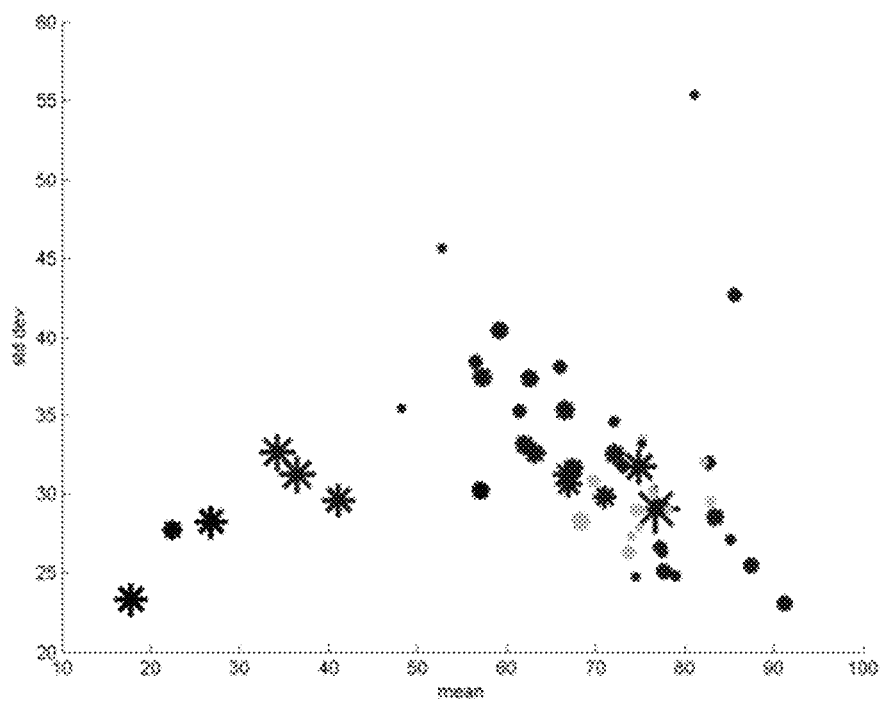
FIG. 3 shows an alternative PED classification of the present invention applied to a set of training data.
Figure 4:
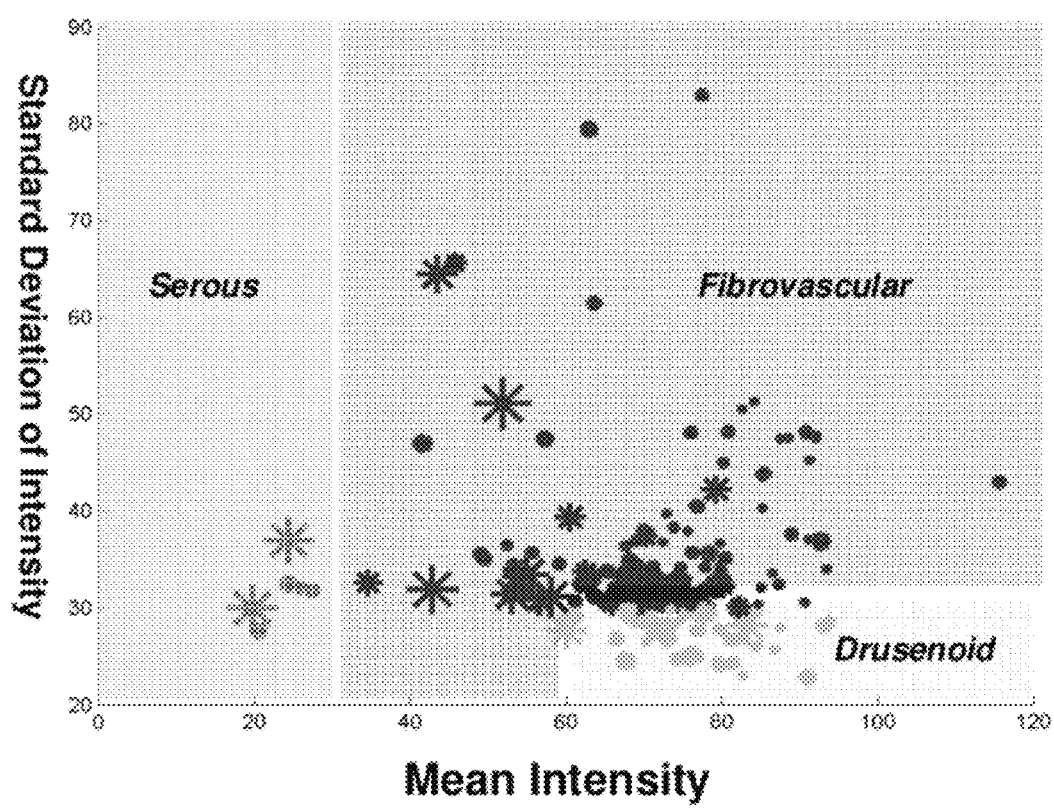
FIG. 4 shows a classification of PEDs based on the present invention.

PED-Level Categorization:

If categorization is based on subsets of the PED intensity data, the categorization can be used in a variety of ways to provide a categorization of the PED in its entirety or a collection of PEDs. Entire PEDs can be categorized, based on the same rules shown for the pixel-level classification, applied to the median or average values of the statistics from each PED. FIGS. 2 and 3 show two such representations for a set of training data in which the median values of the mean A-scan intensity are plotted vs. the median value of the RPE curvature (FIG. 2) and standard deviation (FIG. 3). Blue stars represent fibrovascular PEDs, beige stars represent drusenoid PEDs, and black stars represent serous PEDs. The size of the symbol correlates with PED size. FIG. 4 shows a collection of PEDs from a test data set categorized according to the rules developed on the training data using the same color and sizing conventions. The characterization boundaries (serous, fibrovascular and drusenoid) are overlaid on the plot.

Alternatively, individual PEDs can be classified based on an aggregation of the individual A-scan classifications, by majority vote, for example. In an alternative, if a certain percentage of pixels show fibrovascular content, then the whole PED can be classified as fibrovascular. This allows the sensitivity and specificity of the PED classification to be tuned to account for the sensitivity and specificity of the pixel-level classification.

Figure 5:
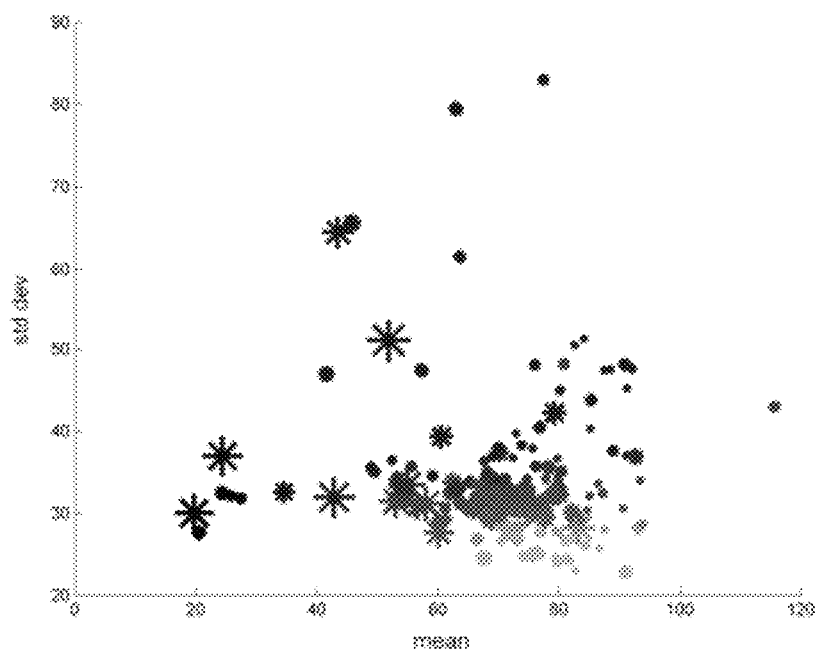
FIG. 5 illustrates a risk index for a collection of PEDs.

The subsets or pixel-level classifications can be used to display the heterogeneity of the PED or generate a risk index for each PED, based on the percentage of pixels that appear to be of one type (i.e. fibrovascular, drusenoid, serous, etc) compared to another. Risk can be based on the fraction of pixels in the fibrovascular category. In an alternative embodiment, the risk could be based on distance in the feature space between PED average statistics and the values of the features for a prototype fibrovascular PED, or on the smallest distance to the boundary used for the fibrovascular categorization. Maps can be created to color code the Risk for each PED. One example of such a risk map is shown in FIG. 5 in which a beige color is used for the most drusenoid PEDs, green shades for partly fibrovascular PEDs, and blue for the strongly fibrovascular PEDs. The colors are darkened to indicate a higher percentage of Serous type pixels. Additional measures of displaying the heterogeneity of the subsets within a single PED can be imagined by someone skilled in the art.

Classifications can be associated with a confidence index related to the distance to the discriminant boundary, or alternatively, related to the distance to the center of the training set for that category, the Mahalanobis distance from the median values of the PED statistics and the nearest category boundary, or a prototypical location defined for that category in the feature space. Bayesian estimates of probability of each category may alternatively be used to assess confidence, or confidence may be assessed by surveying the nearest neighbors in the training set. Confidence can be assessed by pixel then PED, calculating distances separately for each pixel then aggregating the distances, instead of aggregating the metrics first. Confidence could be a percentage of pixels clearly inside a category's boundaries, or an average distance from a category center or prototype.

Figure 6:
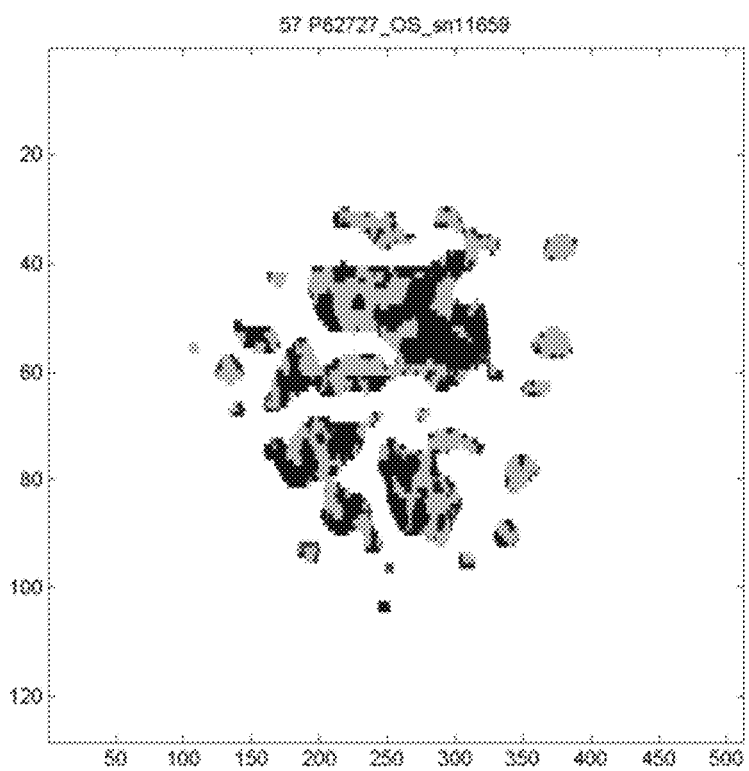
FIG. 6 shows a display of the classification by A-scan in the lateral direction.

Results of the analysis can be displayed in a number of ways. Characteristics of the PED can be evaluated and displayed at the lateral location of each A-scan in an OCT data set as shown in FIG. 6, giving a pixel-level characterization that shows the heterogeneity that may be present within the PED. Here blue indicates A-scans characterized as fibrovascular and beige indicates A-scans that are categorized as drusenoid.

Figure 7:
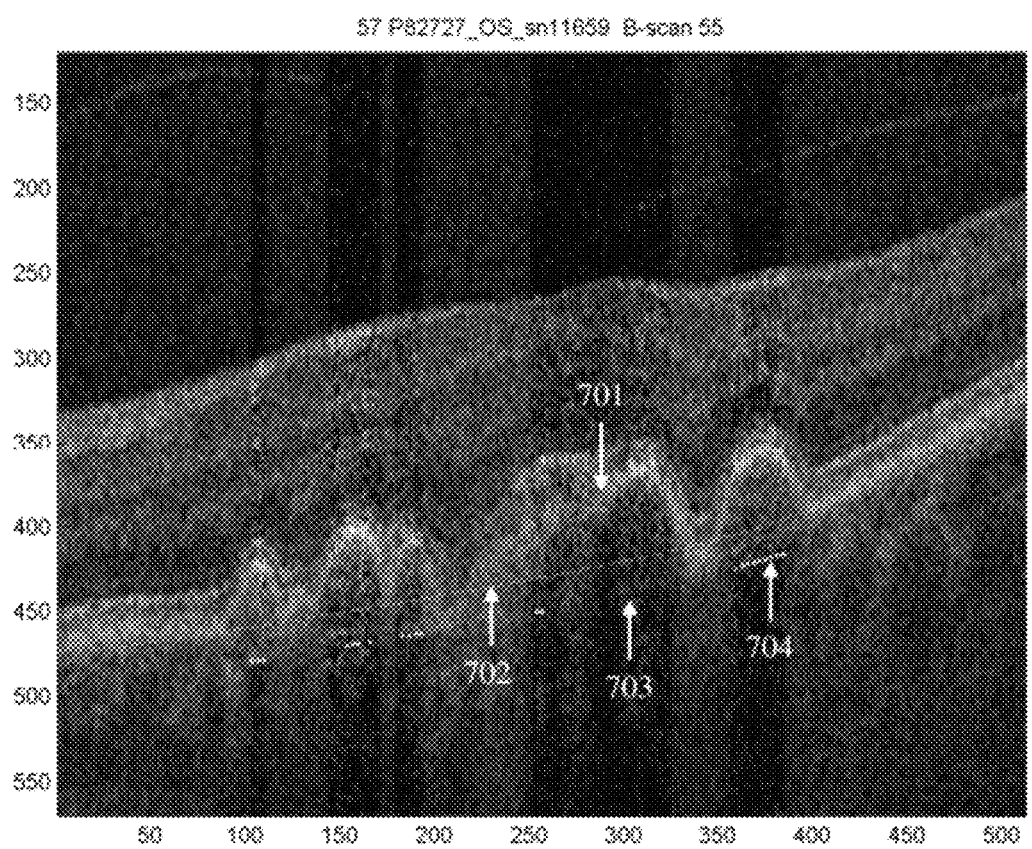
FIG. 7 illustrates the PED classification of individual A-scans within a B-scan.

The results may also be presented in a B-scan view as shown in FIG. 7. Here the normalization of the image data is evident in the changed image intensities along the A-scans that go through a significant depth in the PED. The RPE segmentation 701 is shown in purple and the PED baseline 702 is shown in light blue. A-scans categorized as fibrovascular are shown as blue dots 703 below the PED baseline; A-scans categorized as drusenoid are shown as yellow dots 704.

Measurements of blood flow using OCT data may add useful additional information to the characterization of PED type or risk. Vasculature may be seen more easily with OCT when flow information is used. Abnormal vasculature beneath or inside of PEDs could predict or indicate the presence of neovascularization or Polypoidal Choroidal Vasculopathy (PCV). Several methods have been developed to visualize blood flow using OCT including Doppler, speckle contrast, and phase contrast. Any of these techniques or other OCT angiography techniques could detect the presence of flow within or near a PED and could be used along with one or other representative values based on the intensity or shape of the PED to aid in the characterization of PED type or risk.

Choroidal thickening may help distinguish PCV from AMD. (see for example Chung et al "Choroidal thickness in polypoidal choroidal vasculopathy and exudative age-related macular degeneration" *Ophthalmology*, 118(5):840-5, May 2011). Thus the choroidal thickness in the vicinity of the PED or at a standard location such as the fovea may help with the characterization of the PED. A segmentation of the choroid would clearly require the analysis of the image outside the PED and at locations surrounding the PED, so this is an example of how the analysis does not need to be limited to a strict focus on the PED itself but rather may benefit from contextual information.

Additionally, the location of an abnormality or the relative locations of multiple abnormalities may be used for the characterization. An abnormality's location relative to the fovea, optic nerve head, or other landmark may help determine its type or the risk that it poses to the subject's vision. Similarly, the distribution of multiple abnormalities relative to one another, measured by density of abnormalities, average distance between abnormalities, or other measures of proximity, may help with characterization of lesion type or risk.

This analysis is not limited to the areas of the image inside the PED. Significant information about pigment migration or other reflectivity changes may be found in the RPE or other regions of the image overlying the PED. For example, the variance or other measure of deviation in the reflectivity of this region may be used to identify pigment migration, or an abnormal value of normalized mean reflectivity may indicate more diffuse changes in the retina at the location of the PED. Similarly, the tissue around or below Bruch's membrane (choriocapillaris, choroid, and even sclera) may contain important information about risk for neovascularization or other vasculopathy.

Since PED characterization may benefit from additional information beyond OCT image data, this method may be extended to include data from other imaging modalities. For example a fluorescein or ICG angiography image could be registered to the lateral coordinates of the OCT image data, and characteristics of that image intensity such as local mean value or local deviation could be combined with the OCT-derived information at each lateral location in making classification decisions.

Although various embodiments that incorporate the teachings of the present invention have been shown and described in detail herein, those skilled in the art can readily devise many other varied embodiments that still incorporate these teachings.

The following references are hereby incorporated by reference:

US Patent Publication No. 2011/0299034 Walsh et al. "Optical Coherence Tomography-Based Ophthalmic Testing Methods, Devices and Systems"

Lumbroso et al. "Morphologic Differences, According To Etiology, in Pigment Epithelial Detachments By Means of En Face Optical Coherence Tomography", *Retina* 31 (3): 553-558 2011.

Hartnett et al. "Classification of retinal pigment epithelial detachments associated with drusen", *Graefes Arch Clin Exp Ophthalmol*. 1992; 230(1):11-9.

Khanifar et al. "Drusen ultrastructure imaging with spectral domain optical coherence tomography in age-related macular degeneration", *Ophthalmology*. 2008 November; 115(11): 1883-90

Gregori et al. "Imaging drusen with spectral domain optical coherence tomography" Invest Ophthalmol Vis Sci 49(E-Abstract 4234) 2008).

Chung et al "Choroidal thickness in polypoidal choroidal vasculopathy and exudative age-related macular degeneration" *Ophthalmology*, 118(5):840-5, May 2011.

Lee et al. "Automated Classification of Pigment Epithelial Detachments using Optical Coherence Tomography" 2011 ARVO Poster Abstract Program #1317, Poster #A254.

What is claimed is:

1. A method of analyzing an abnormality in the retinal layers of the eye, said method comprising:
   collecting three dimensional optical coherence tomography (OCT) intensity data of the retinal layers of the eye including the abnormality;
   segmenting the OCT intensity data to identify the boundaries of the abnormality;
   determining a first representative value associated with the identified abnormality;
   determining a second representative value associated with the identified abnormality, said first and second representative values being selected from the following characteristics of the identified abnormality:
      average intensity of the data within the boundaries of the abnormality;
      uniformity of the intensity of the data within the boundaries of the abnormality;
      shape of the abnormality;
      size of the abnormality;
      blood flow within the abnormality; and
      location of the abnormality;
   provided, however, that the characteristic selected for the first representative value is different from the characteristic selected for the second representative value;
   classifying the abnormality based on the first and second representative values using predetermined criteria; and
   displaying or storing the classification.

2. A method as recited in claim 1, wherein the abnormality is a pigment epithelial detachment (PED).

3. A method as recited in claim 2, wherein the determining and classifying are carried out on subsets of the intensity data within the boundaries of the PED.

4. A method as recited in claim 3, wherein the subsets are A-scans contained within the identified PED boundaries.

5. A method as recited in claim 3, wherein the first representative value is the mean of the intensity for the portion of the A-scan within the PED boundary and the second representative value is the standard deviation of the intensity for the portion of the A-scan within the PED boundary.

6. A method as recited in claim 3, wherein the first representative value is the mean of the intensity for the portion of the A-scan within the PED boundary and the second representative value is the curvature of the RPE.

7. A method as recited in claim 4, further comprising calculating a single index for each PED by combining the classifications for the A-scans within the identified PED boundaries.

8. A method as recited in claim 7, wherein the classifications are displayed based on the location of the A-scans.

9. A method as recited in claim 3, further comprising calculating a confidence index for the classification.

10. A method as recited in claim 3, further comprising calculating a fibrovascular PED risk index based on the percentage of the subsets within a PED that are classified as fibrovascular.

11. A method as recited in claim 1, wherein the predetermined criteria are developed using a collection of training data.

12. A method as recited in claim 2, wherein the PED is classified as one of: serous, fibrovascular, and drusenoid.

13. A method as recited in claim 2, wherein the predetermined criteria have a higher sensitivity for fibrovascular PEDs.

14. A method as recited in claim 2, wherein the the first representative value is selected from: mean of intensity, median of intensity, trimmed mean intensity and weighted mean intensity and wherein the second representative value is selected from standard deviation of intensity, RPE curvature, size of the abnormality, and choroidal thickness.

15. A method as recited in claim 1, further comprising normalizing the data prior to the classifying.

16. A method of characterizing regions of pigment epithelial detachment (PED) within the eye of a patient based on image data obtained from an optical coherence tomography (OCT) system, said method comprising the steps of:
identifying tissue regions within the image that correspond to PEDs;
determining a first representative value associated with the average intensity of the data in each identified region;
determining a second value associated with each identified region, said second representative value being selected from one of uniformity of the intensity of the region or a geometric attribute of the region;
classifying the type of PED in the identified region based on the first and second representative values; and
displaying or storing the results of the classification.

17. A method as recited in claim 16, wherein the second value is based on the standard deviation of the intensity of the identified region.

18. A method as recited in claim 16, wherein the second value is based on the curvature of the identified region.

19. A method as recited in claim 16, wherein the display is arranged to identify both the classification of the identified region as well as the position within the eye where the region is located.

20. A method as recited in claim 16, wherein the identified region is classified as one of: serous, fibrovascular, and drusenoid.

21. A method as recited in claim 1, wherein the average intensity is defined as one of the mean of intensity, the median of intensity, the trimmed mean intensity and the weighted mean intensity.

22. A method as recited in claim 2, wherein the first representative value is a characteristic that reflects the presence of blood flow within the PED and the second representative value is a characteristic of the average intensity, the uniformity of intensity or the shape of the PED.

23. A method as recited in claim 16, wherein the first representative value is defined as one of the mean of intensity, the median of intensity, the trimmed mean intensity and the weighted mean intensity.

* * * * *